United States Patent [19]

Wess et al.

[11] Patent Number: 5,133,338
[45] Date of Patent: Jul. 28, 1992

[54] MEDICAL LITHOTRIPSY WORK STATION

[75] Inventors: Othmar Wess; Roland Denk, both of Munich; Karl-Heinz Restle, Tettnang; Herbert Weiler, Alling, all of Fed. Rep. of Germany

[73] Assignee: Dornier Medizin Technik GmbH, Fed. Rep. of Germany

[21] Appl. No.: 187,586

[22] Filed: Apr. 28, 1988

[30] Foreign Application Priority Data

Mar. 4, 1988 [DE] Fed. Rep. of Germany ....... 3714397

[51] Int. Cl.$^5$ ............................................. A61B 17/22
[52] U.S. Cl. ............................... 128/24 EL; 378/195; 378/197
[58] Field of Search ................................. 128/24 EL; 378/195-198, 209; 269/322-328

[56] References Cited

U.S. PATENT DOCUMENTS

| | | | |
|---|---|---|---|
| 4,148,472 | 4/1979 | Rais et al. | 378/209 |
| 4,298,801 | 11/1981 | Heitman et al. | 378/196 |
| 4,796,613 | 1/1989 | Heumann | 128/74 EL |
| 4,829,257 | 4/1989 | Grasser | 128/24 EL |
| 4,821,729 | 4/1989 | Makofski et al. | 128/24 EL |

Primary Examiner—Kyle L. Howell
Assistant Examiner—Scott R. Akers
Attorney, Agent, or Firm—R. H. Siegemund

[57] ABSTRACT

A medical work station has a central post; a vertically adjustable and pivotable mount on the post; a multi part rest having a head portion which is mounted to the mount for the rest to extend in various horizontal positions from the post; an X-ray station is pivotable mounted on a second post being offset from the central post, the X-ray station including equipment which, upon pivoting, covers a range that coincides with a limited position range of the rest as pivotably mounted on the central post; a stand for shock wave equipment is positioned so that the rest can be placed above it or has a particular position in relation thereto; and an ultrasonic equipment mounted on and including a multi-linked arm arrangement having a mounting part mounted on the rest mount.

14 Claims, 3 Drawing Sheets

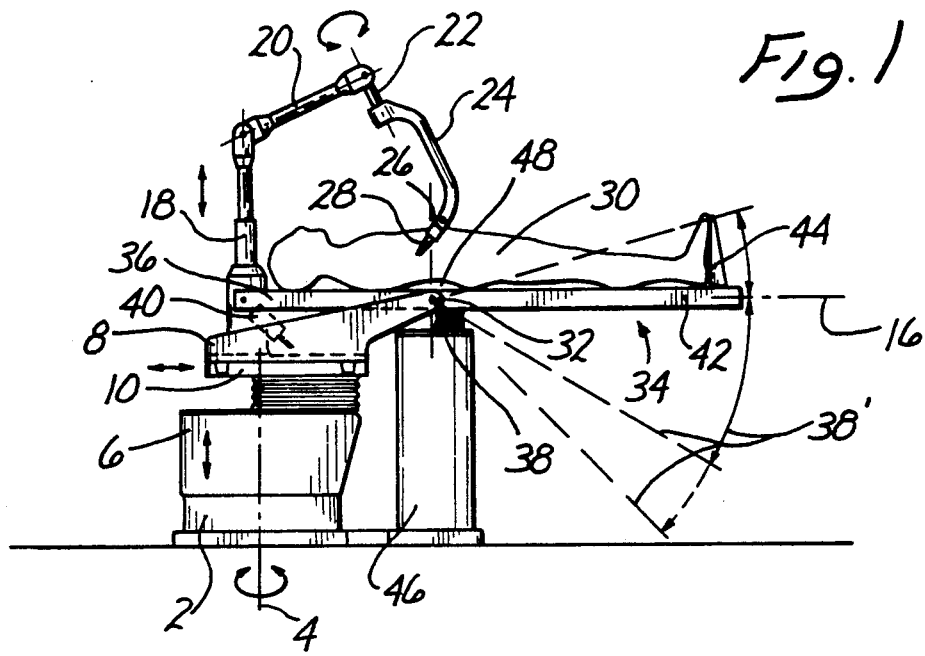
Fig. 1
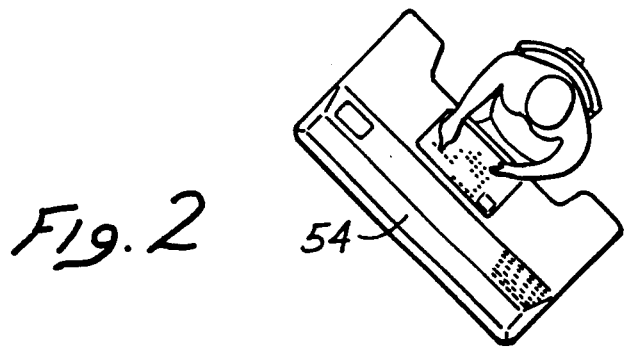
Fig. 2
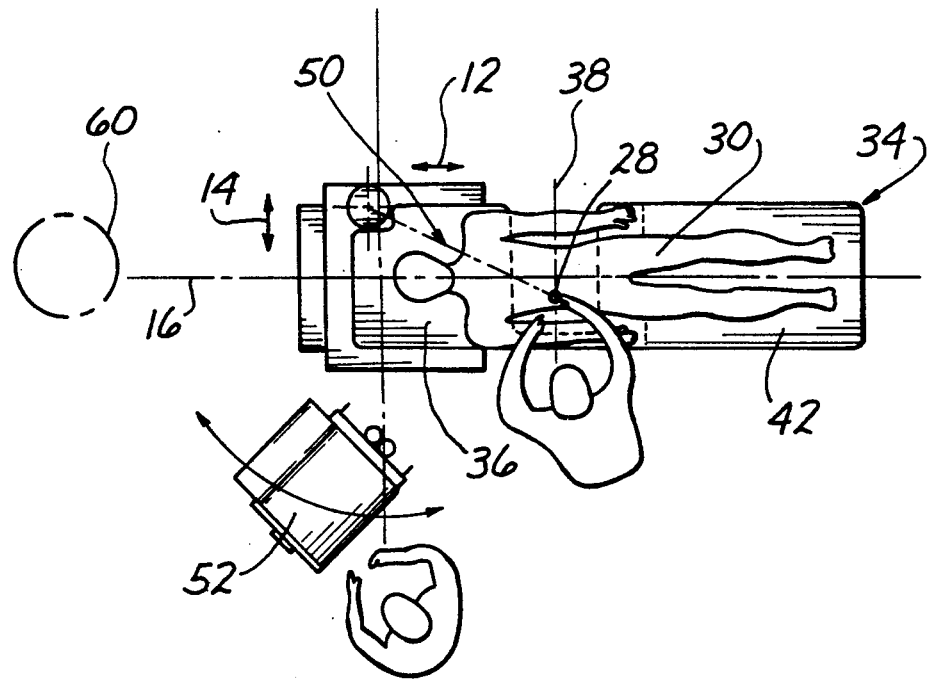

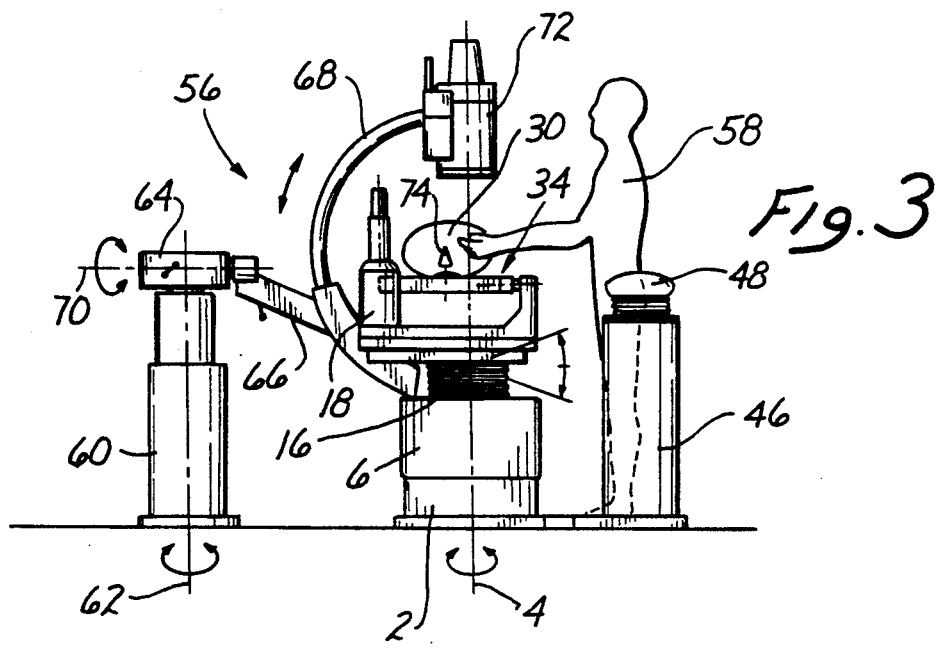
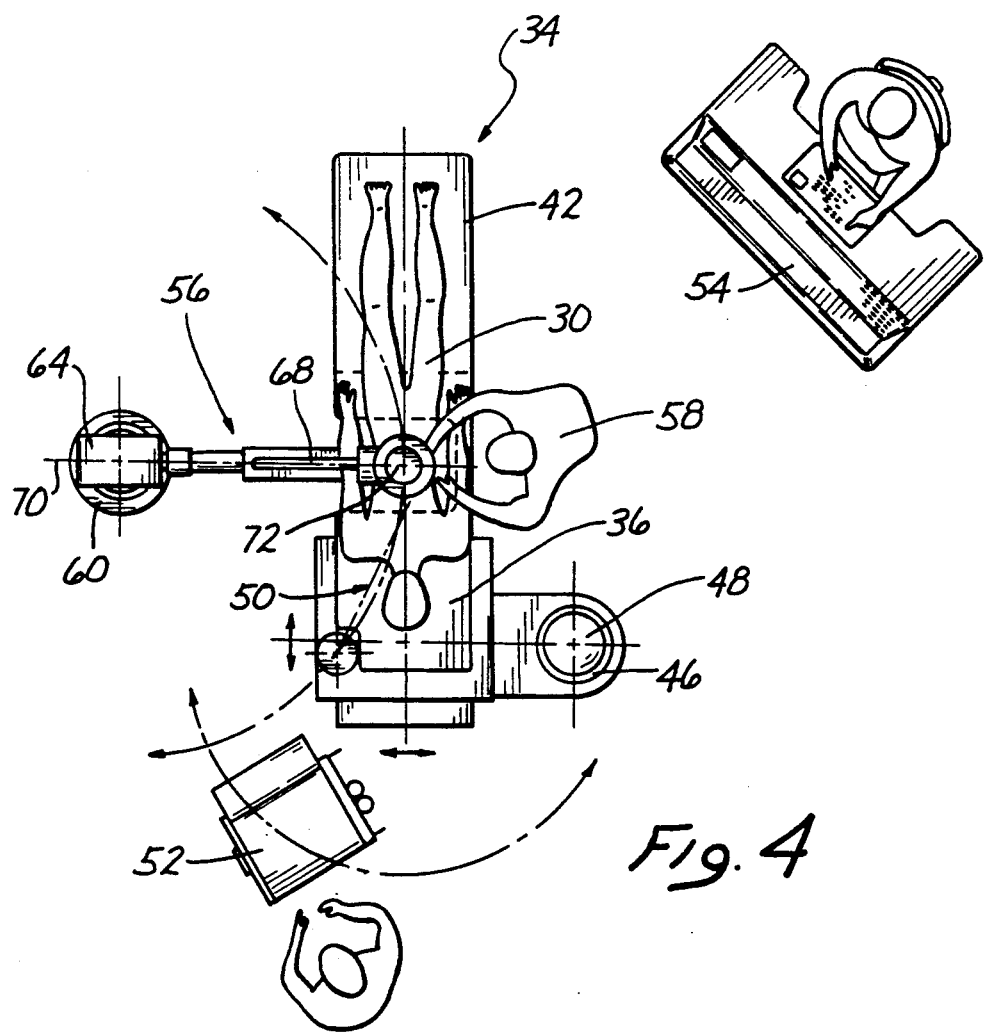

MEDICAL LITHOTRIPSY WORK STATION

BACKGROUND OF THE INVENTION

The present invention relates to a universal medical work station, particularly for controlling and conducting shock wave therapy involving the comminution of kidney stones, gall stones, and concrements of like nature, under further utilization of X-ray and ultrasonic diagnostics and locating practice, as well as treatment, but the station should be useful also for general checkups, tests, and the like, particularly of a urological nature.

Kidney stone and gall stone lithotripsy is a field of increasing importance. It involves pre-treatment, treatment, and post-treatment phases requiring certain manipulations of the patient. For example, the pre-treatment phase includes the detection and locating of the concrements to be comminuted, followed by the treatment which requires very accurate positioning of the destroying equipment vis-a-vis the object being comminuted, and the post-operative phases includes certain check-ups and the like, in order to see and to evaluate the success of the treatment.

In each of these phases it is required to have the patient in a particular position and he or she has to be manipulated, particularly as far as positions are concerned. The same is true for any general, urological check-up and treatment, which also require the patient to be analogously placed in different positions. Also, in the case of general urological tests, the application of X-ray and of ultra sonic equipment is common practice. In order to treat the various body parts from many even directions, it is necessary to relocate the patient. This is, for example, the case following immediately a process of destroying, for example, kidney stones. Here, an X-ray is to be taken in order to determine whether or not the treatment was successful and can, thus, be terminated. The equipment for taking the X-ray should be spatially separated from the lithotriptor and this, in turn, requires relocating of the patient. Particular problems exist in the fact that X-ray equipment and shock wave equipment are generally quite far apart from each other in order to avoid physical interference. Hence, relocating of the patient, possibly several times, is necessary. Broadly speaking, in the past it was merely recognized that extensive multiple equipment is required, e.g. for lithotripsy; each doing its own thing. But it must be recognized that the procedure is, in fact, a continuous one and multiple steps are to be taken in a coordinated fashion, without mutual interference.

DESCRIPTION OF THE INVENTION

It is an object of the present invention to provide a new and improved work station for lithotripsy permitting X-ray and/or ultrasonic positioning and locating devices, as well as shock wave generators, but also other, e.g. urological equipment to be placed in such a mutual association that, on one hand, the various pieces of equipment are not, so to speak, in the way of each other while, on the other hand, compactness of the arrangement ensures that the equipment is basically in the same station so that the patient does not have to be relocated from the action area and zone of one piece of equipment to the action zone of another piece of equipment.

In accordance with the preferred embodiment of the present invention, it is suggested to arrange ultrasonic equipment, X-ray equipment, shock wave generators, and additional urological equipment necessary for lithotripsy and urological tests around a central post and that a rest for the patient is pivotable on a vertical axis and extends, in addition, from that post, in a horizontal direction. The patent rest is put in different orientations from the vertical axis of that post to be put directly into different action zones of diagnostic/treatment equipment or into zones into which such equipment can be put also, whereby different action zones, different zones of placement, and differrent rest orientation establish different kinds of association in terms of orientation between equipment and patient.

It can thus seen that the inventive work station basically includes an arrangement of equipment wherein, on one hand, locating and diagnostic equipment is spatially separated from therapeutic equipment, but both types of equipment are spatially associated such that the transport of the patient to the individual pieces of equipment requires merely a pivoting of the rest on which the patient lies. Therefore, on pivoting this rest through a certain range, the patient assumes a plurality of different positions while remaining at rest and without being himself or herself physically located or relocated. The pieces of equipment are associated with the patient in and along on that pivot range, whereby the equipment may have its own range of pivoting and extension. The patient will not change position on the rest, once that position has been assumed, and he/she is subject to retention, for example, by strapping in so that the various limbs and body parts do not change position in relation to that rest, and to the equipment. This is particularly important when the patient has been anesthetized.

The arrangement is basically of a modular design, and is comprised essentially of four major components. (i) There is a centrally arranged post being the carrier for the patient rest. (ii) There is an ultrasonic locating equipment mounted to that post. (iii) There is X-ray equipment, pivotally with the pivot axis being spaced-apart. And (iv) there is a shock wave generator, including a coupling cushion, being the third major component that is mounted close to that post. The pieces of equipment themselves remain as they have been positioned except that, of course, within a certain range each piece of equipment is subject to adjustment of orientation, spacing, location, and so forth. But, as a whole, the pieces of equipment as mounted remain invariable as far as the post is concerned; but in some instances, they pivot on their own axis, while the rest itself is pivotal on that post. This means as that doctor or any other attending physician, other medical and technical personnel have, throughout the operation and procedure, free access to the patient. For example, the anesthetist will have a fixed position in the treatment area because pivoting is preferably carried out such that the head of the patient remains right on or near the post. In other words, the rest is constructed such that pivoting will not shift the head; the axis of pivoting runs through or close to the head.

Upon attempting to comminute concrements, the concrements have to be located in the body of the human being. For this one can use the plurality of different locating devices and even systems. Basically, the arrangement above requires that there be an ultrasonic locator and an X-ray device. This, in accordance with current belief, is the best combination for locating, kidney stones and gall stones. This dual equipment provides a highly advantageous compromise as far as accuracy of locating and X-ray load on the patient is concerned. The X-ray, of course, requires free selection of the plane in which the X-ray is to be taken. Nothing precludes the use of elevational adjustment of upper and lower table positions in obtaining variations in the utilization of the X-ray equipment.

The inventive work station is believed to be vary useful for the following kinds of diagnostic and therapeutic purposes: kidney stone comminution; gall stone comminution; general ultrasonic diagnostics; general X-ray diagnostics, including particularly standard tests as practiced in urology; catheter insertion under X-ray controls; X-ray cassette pictures, as is used in urology and diagnostics of the upper abdomen; general X-ray treatment; percutaneous left or right-hand litholapaxy; ultrasonic and/or X-ray controlled punctures; percutaneous litholapaxy as controlled by ultrasonics.

DESCRIPTION OF THE DRAWINGS

While the specification concludes with claims particularly pointing out and distinctly claiming the subject matter which is regarded as the invention, it is believed that the invention, the objects and features of the invention, and further objects, features, and advantages thereof will be better understood from the following description taken in connection with the accompanying drawings in which:

FIG. 1 is a side view in a somewhat schematic fashion, of a work station in accordance with the preferred embodiment of the present invention for practicing the best mode thereof and showing particularly ultrasonic locating equipment as well as a shock wave generator;

FIG. 2 is a top view of the device shown in FIG. 1 with the additional showing of a control console;

FIG. 3 is a side view of the same work station, but used for X-ray diagnostics, the patient being in a different position of orientation;

FIG. 4 is a top view of the device shown in FIG. 3, also shown with operator control desk;

Proceeding, now, to the detailed description of the drawings, FIG. 1 illustrates, as stated, a side view of an inventive work station; here, and in all figures, the central part is a centrally located post 2 around which, and on which the various pieces of equipment are being arranged. First of all, particularly on the very top of this post 2 is arranged a rotatable or pivotable part 6, being particularly pivotable about the vertical axis 4. This particular part 6 will serve as a rest mount and for this reason is hereinafter referred to as pivot mount 6. This mount 6 may be capable of covering about three-fourths of a circle, that means about 270 degrees. In addition, however, this part 6 can be adjustable in up or down direction, i.e. on and along the pivot axis 4.

Figure 5:
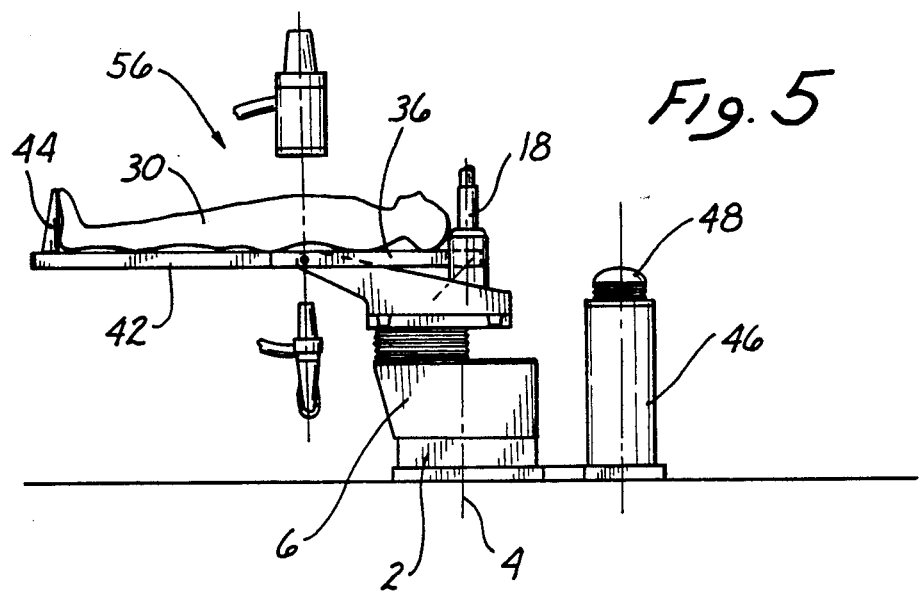
FIG. 5 is a side view of still the same work station and using the same X-ray equipment, but in a changed position for the patient.

A carrier arm 8 with bottom plate 10 is mounted to the pivot mount 6. This carrier arm 8 can be shifted in a horizontal direction. This horizontal direction is variable with pivoting on axis 4, but can be deemed to be a direction composed of an X axis direction 12 and a Y axis direction 14 in a stationary coordinate system. In addition, tilting is made possible, around the longitudinal axis 16 (see particularly FIG. 2) of this carrier arm 8. The patient rest 34 to be described more fully below, is mounted on arm 8.

Another carrier 18 is mounted to the bottom plate 10, it extends basically in a vertical direction but has hinged to it a part 20, to which is connected an arm 22, which, in turn, carries looped arm 24 for manipulating the pieces of equipment arranged at the end of the arm 24. Any length extension or contraction can be obtained through telescopic arrangement of the various members. The end arm 26 of this arrangement is the holder that carries an X-ray head 28. The multiple hinging adjustability and variability of positioning of the various arms 18, 20, 22, 24, 26, in relation to each other permits the ultrasonic head 28 to attain a highly universally variable position. In fact, then, every part of the human body, i.e., of a patient 30 lying on the rest 32, can be reached through the equipment 28 mounted on this arm arrangement.

A particular hinge 32 is arranged at the horizontal carrier arm 8 and the patient rest 34 is mounted thereto. This rest is constructed in the illustrated version from three parts. The first part 36 is directly connected to the arm 8 through a shaft 38, having a horizontal axis. The entire rest 34 can be pivoted or tilted about this axis 38. The angular indicators 38' represent this tilting. This means that the head and foot part of the patients 30 can either be placed on the same level or in different ones, depending on the degree of tilting. However, the patient will remain stretched out on the rest 34 and arm 8, and thus, remains situated basically in one plane, even though that plane is tilted.

The tilting of the rest 34 and the plane of reset obtains through a motor 40. Basically, the head of the patient, shoulder, the arm, and the pelvis of the patient are placed on the part 36. A second rest part 42 is connected to the first part 36 and is provided as a rest for the legs. The feet of the patient will be supported by the third rest part 44, being connected to part 42 accordingly. The connection of part 42 to the part 36 may be of the simple plug-in variety.

A shock wave generator 46 is situated next to the post 2. The shock wave generator itself includes, or is constructed as a round pillar with a coupler cushion 48 arranged on the upper end. This coupling cushion 48 fits into a gap in the first part 36 of the rest 34, so that cushion 48 can in fact be juxtaposed to the body of the patient without interpositioning of any possible interfering part.

FIG. 2 illustrates a constellation and configuration of the work station as seen from above, when the patient is above the shock wave generator 46. Here, then, one can readily recognize the position of the patient 30 on the two parts 36 and 42. The arms 20 through 26 with ultrasonic head 28 can be deemed to pertain to ultrasonic equipment 50 generally, which an attending physician 31 manipulates for diagnostic purposes. The ultrasonic image provided by means of the equipment 28 is made visible on a monitor 52 being likewise movable and positionable for ease of access. Control and monitoring of the entire equipment is carried out from the desk 54. Here, then, of course, positioning, control, monitoring, and the like is electronically controlled with suitable indications provided at a suitable display panel or panels being part of that desk 54.

FIGS. 3 and 4 illustrate a changed rest position, in the work station still using X-ray equipment 56. This piece of equipment is not shown completely in FIG. 1 or 2, only a mounting post 60 is shown in FIG. 2. The entire X-ray equipment is to be considered to be present. In accordance with FIG. 3, now, this X-ray equipment 56 has been pivoted into a range of the patient rest, while the patient rest 34 was shifted by 90 out of the shock wave treatment position. The arms 18 and so forth simply have been removed or pivoted out of the way. The pillar or post for mounting the shock wave equipment 46, together with the coupling cushion 48, can be seen in FIG. 3 to the right of the attending X-ray diagnosing person 58. The standing post 60 is provided in line with the rest when in the ultrasonic action zone (FIGS. 1, 2), post 60 has an upper part 64 which is pivotable about a vertical axis 62 of the post 60, covering a range of at least 180. This mounting part 64 carries the X-ray equipment 56. Moreover, there is a holder 66 provided on this mount 64 for mounting, in turn, an arch or loop-shaped or quasi-loop-shaped arm 68. The holder 66 can be pivoted about an axis 70, which extends perpendicular to the axis 62. The arch 60' defines an action zone for the X-ray equipment. The patient is out of that action zone when in the position of FIGS. 1, 2.

The X-ray equipment 72 can be moved along and on the arc-shaped arm 68 in a relation to the longitudinal axis 16 so that all sides of the body of the patient 30 become accessible to the X-ray equipment and can, therefore, be subjected to X-raying. In addition, it can be seen that the patient rest 34 can be tilted around the longitudinal axis 16. The purpose of tilting may be to avoid shading of the concrement by the spine 74, for example, of the patient 30 or by other obstacles.

Figure 6:
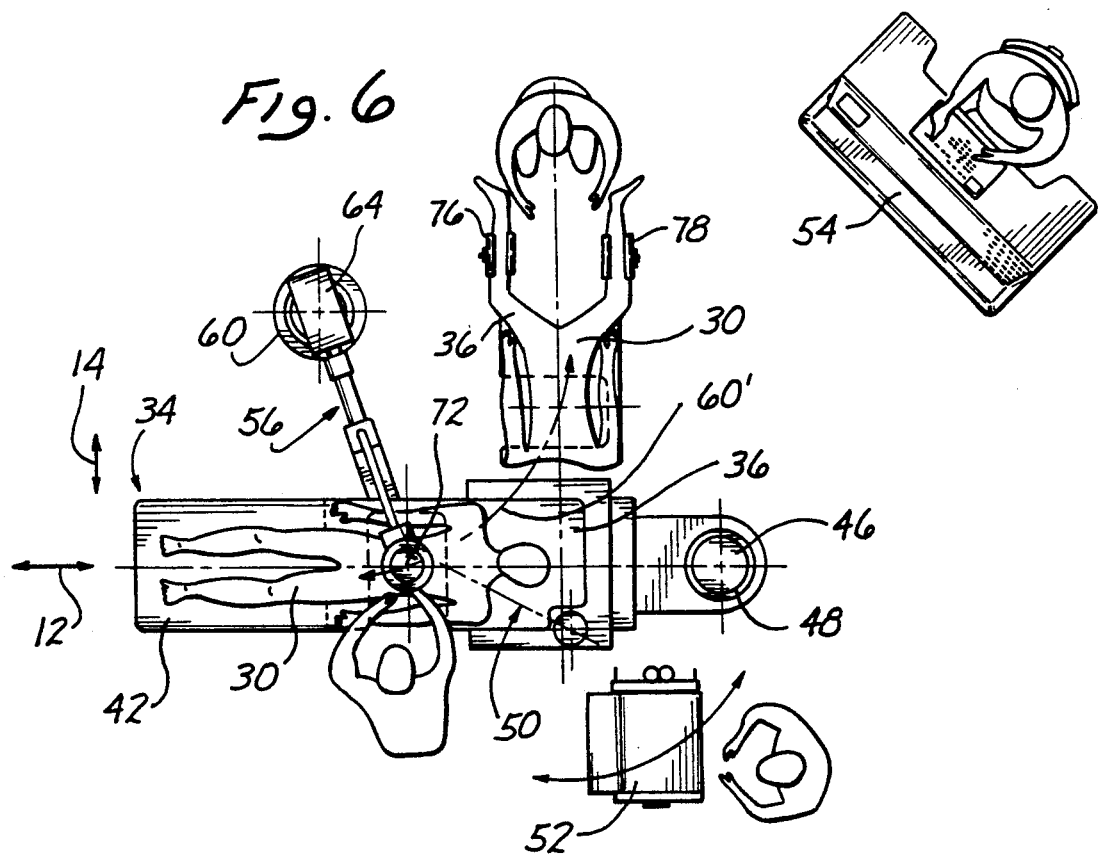
FIG. 6 is a top view of the arrangement shown on FIG. 5, also with an additional control desk and illustrating additionally the utilization of the station for a urological diagnostic check-up.

FIGS. 5 and 6 show the work station again, respectively, in side and top elevation, and with a still different position and orientation of the patient rest and of the patient him/herself, with a partial view of the X-ray equipment 56. The adjustability of the structure shown in FIG. 3 remains as is. In fact, a comparison of FIGS. 6 and 4 shows the great versatility in aligning the action zones of the bed (rest) 34, and of the X-ray equipment (60').

FIG. 6 shows particularly that the patient rest 34 is pivoted by 180 out of the position shown in FIG. 2, assumed on shock wave treatment. Here, then, a pivoting by 90 into the opposite direction of the patient 30 will place the patient in the range of the X-ray equipment 56. Separately, one can see that the second or middle part 42 of the rest 34 is infact replaced by two separate leg support elements 76 and 78, which are individually plugged into the head part 36 of the patient rest 34. This particular feature permits an attending physician to provide stantard urological tests, diagnosis, treatment, and the like.

The invention is not limited to the embodiments described above, but all changes and modifications thereof not constituting departures from the spirit and scope of the invention are intended to be included, such as suitable recording devices for the X-ray and/or ultrasonic imaging equipment.

We claim:
1. Medical work station comprising:
a central post having a vertical axis;
a vertically adjustable and pivotable mount being mounted on the post for vertical adjustment and pivoting about the vertical axis by 270°:
a multi-part rest having a head portion mounted to said mount so that the vertical axis runs through the head portion and for the rest to extend in various horizontal positions from the past as the mount is pivoted about the vertical axis;
a second post positioned next to the central post and having a vertical axis;
an X-ray station means pivotable mounted on said second post and in an offset position from the central post, the X-ray station including equipment which, upon pivoting about the axis of the second post, covers a range that (coincides) overlaps with a limited position and pivot range of the rest as pivotably mounted on the central post, so that a patient when on the rest can be moved into and out of a range covered by the X-ray station as pivoted about the second post;
a stand (for) with shock wave equipment positioned laterally offset from the central post so that upon pivoting of the mount the rest and a patient thereon, is positioned (above it or has a particular position in relation thereto) adjacent to the shock-wave equipment of the rest with the patient thereon can be pivoted away from the shockwave equipment; and
(an ultrasonic equipment mounted on and including) a multi-linked arm arrangement having a mounting part mounted on said mount for pivoting therewith, there being ultrasonic equipment mounted on the arm arrangement.

2. Station as in claim 1, the mounting means further pivotable on a horizontal axis.

3. Station as in claim 1, there being a bottom plate on the mount for providing the mounting of the rest on said mount.

4. Station as in claim 1, said rest having a window, said stand including a coupling cushion projecting into the window.

5. Station as in claim 2, the rest being tiltable about a longitudinal horizontal axis transverse to said horizontal axis.

6. Work station as in claim 1, said X-ray station having means on said second post for tilting about a horizontal axis.

7. Medical work station comprising:
a central post having a vertical axis:
a mount on the central post for pivoting about a vertical axis by at least 270°:
a patient rest having a head part (positioned) mounted on said (post) mount with said head part of the rest mounted thereon for rotating and pivoting the rest as a whole about said vertical axis (being in a central position) when said mount is pivoted about the vertical axis, said axis running through the head part of the rest; and
a plurality of diagnostic and/or therapeutic equipment including shock wave generator adapted for the comminution of concrements in the body of a patient when on the rest; ultrasonic equipment for locating concrements, and X-ray equipment also adapted for locating concrements in the body of the patient;
said equipment being individually permanently mounted in spaced position in relation to each other and in close relation to and around said post and being movable in relation thereto to obtain positioning of each of the pieces of equipment into and out of a particular treatment and action zone and (zone) range while, in addition, said rest upon being pivoted about the vertical axis of the post is being pivoted into and out of any of these individual zones and ranges of the equipment.

8. Work station as in claim 7, (said post including a stationary post part and a mounting element on the post provided for shifting up and down as well as pivoting on the stationary post, said rest being mounted to said mounting element;) and means on said head part for tilting said rest about a generally horizontal longitudinal axis.

9. Work station as in claim 7, said shock wave generator being provided with a coupling cushion and being positionable to be placed underneath said rest, there being an opening in the rest for a coupling the cushion to the patient from below.

10. Work station as in claim 7, said ultrasonic locating equipment being mounted on a multiple link of hinged arms, basically extending from a vertically mounted pivotable arm element that is mounted to said rest moun(ting element).

11. Work station as in claim 7, said X-ray equipment being physically separated from said post, and mounted for tilting on a separate vertical axis.

12. Work station as in claim 11, there being loop-shaped arm for holding the X-ray equipment being pivoted into and out of a range as defined by the position of the rest.

13. Work station as in claim 7, said X-ray equipment being mounted for multiple tilting.

14. Medical work station comprising:
a central post having a vertical axis;
a vertically adjustable and pivotable mount being mounted on the post for vertical adjustment and pivoting about the vertical axis by 270° d said mount in addition being adjustible in the horizontal;
a multi-part rest having a head portion mounted to said mount so that the vertical axis runs through the head portion and for the rest to extend in various horizontal positions from the post as the mount is pivoted about the vertical axis;
a second post permanently positioned next to but offset from the central post and also having a vertical axis;
a loop shaped arm mounted for pivoting about the vertical axis of the second post;
an X-ray station mounted on said second post the X-ray station including X ray equipment which, upon pivoting about the axis of the second post, covers a range that overlaps with a limited position and pivot range of the rest as pivotably mounted on the central post, so that a patient when on the rest can be moved into and out of a range covered by the X-ray station as pivoted about the second post;
a stand with shock wave equipment positioned laterally offset from the central post so that upon pivoting of the mount the rest and a patient thereon is positioned adjacent to the shockwave equipment or the rest with the patient thereon can be pivoted away from the shockwave equipment; and
a multi-linked arm arrangement having a mounting part mounted on said mount for pivoting therewith about the vertical axis of the central post, there being ultrasonic equipment mounted on the arm arrangement.

* * * * *